(12) United States Patent
Yu et al.

(10) Patent No.: US 10,076,306 B2
(45) Date of Patent: Sep. 18, 2018

(54) ELECTRIC TOOTHBRUSH WITH ULTRASOUND SENSOR

(71) Applicant: Ning Chen, Katy, TX (US)

(72) Inventors: Long Yu, Gainesville, FL (US); Bo Wang, Sugar Land, TX (US); Ning Chen, Katy, TX (US)

(73) Assignee: Ning Chen, Katy, TX (US)

( * ) Notice: Subject to any disclaimer, the term of this patent is extended or adjusted under 35 U.S.C. 154(b) by 1 day.

(21) Appl. No.: 15/388,344

(22) Filed: Dec. 22, 2016

(65) Prior Publication Data

US 2018/0177489 A1    Jun. 28, 2018

(51) Int. Cl.

| | |
|---|---|
| *A61B 8/12* | (2006.01) |
| *A61B 8/00* | (2006.01) |
| *A46B 9/04* | (2006.01) |
| *A46B 15/00* | (2006.01) |
| *A46B 5/00* | (2006.01) |
| *A61C 17/22* | (2006.01) |
| *A61B 5/00* | (2006.01) |
| *A61B 8/08* | (2006.01) |

(52) U.S. Cl.
CPC .......... *A61B 8/4427* (2013.01); *A46B 5/0095* (2013.01); *A46B 9/04* (2013.01); *A46B 15/0022* (2013.01); *A46B 15/0028* (2013.01); *A61B 5/4547* (2013.01); *A61B 5/6887* (2013.01); *A61B 8/0875* (2013.01); *A61B 8/4411* (2013.01); *A61B 8/5223* (2013.01); *A61B 8/565* (2013.01); *A61C 17/222* (2013.01)

(58) Field of Classification Search
CPC ... A61B 8/4427; A61B 5/4547; A61B 5/6867; A61B 8/0875; A61B 8/4411; A61B 8/5223; A61B 8/565; A46B 5/0095; A46B 9/04; A46B 15/0022; A46B 15/0028; A61C 17/222

See application file for complete search history.

(56) References Cited

U.S. PATENT DOCUMENTS

| | | | | |
|---|---|---|---|---|
| 4,131,967 | A * | 1/1979 | Northemann | A46B 5/00 15/167.2 |
| 4,137,593 | A * | 2/1979 | Porper | A46B 5/02 15/167.2 |
| 9,724,001 | B2 * | 8/2017 | Dykes | A61B 5/02427 |
| 9,811,636 | B2 * | 11/2017 | Dykes | G06F 19/345 |
| 2002/0152563 | A1 * | 10/2002 | Sato | A46B 9/026 15/22.1 |
| 2009/0083924 | A1 * | 4/2009 | Shepherd | A46B 5/0095 15/105 |
| 2011/0010875 | A1 * | 1/2011 | Iwahori | A46B 15/0006 15/22.1 |
| 2011/0010876 | A1 * | 1/2011 | Iwahori | A46B 15/0002 15/22.1 |

(Continued)

*Primary Examiner* — Nicholas Lucchesi
(74) *Attorney, Agent, or Firm* — SZDC Law P.C.

(57) ABSTRACT

An electric toothbrush includes a handle and a brush head attached to one end of the handle. The brush head includes a bristle unit and an ultrasound sensor. The bristle unit cleans teeth and the ultrasound sensor acquires ultrasound data of the teeth. A portable tooth decay detection device includes a handle and an ultrasound sensor attached to one end of the handle. The ultrasound sensor emits and receives ultrasound signal at a frequency of higher than 20 KHz and acquires ultrasound data of teeth.

1 Claim, 7 Drawing Sheets

(56) References Cited

U.S. PATENT DOCUMENTS

| | | | |
|---|---|---|---|
| 2011/0296643 A1* | 12/2011 | Shepherd | A46B 5/0095 15/167.1 |
| 2011/0312278 A1* | 12/2011 | Matsushita | H04L 12/40013 455/66.1 |
| 2012/0295216 A1* | 11/2012 | Dykes | A61C 17/22 433/27 |
| 2013/0080295 A1* | 3/2013 | Dykes | A61C 17/221 705/27.1 |
| 2013/0091642 A1* | 4/2013 | Dykes | A46B 15/0008 15/22.1 |
| 2013/0333134 A1* | 12/2013 | Herr | A46B 9/045 15/167.2 |
| 2015/0088538 A1* | 3/2015 | Dykes | A61C 17/26 705/2 |
| 2016/0220013 A1* | 8/2016 | Barnes | A46B 9/04 |
| 2017/0020277 A1* | 1/2017 | Barnes | A61C 17/3436 |
| 2017/0100223 A1* | 4/2017 | Silverberg | A61C 17/228 |

* cited by examiner

ELECTRIC TOOTHBRUSH WITH ULTRASOUND SENSOR

BACKGROUND OF THE INVENTION

Field of the Invention

The present invention relates to an electric toothbrush with an ultrasound sensor and the use thereof.

Discussion of the Related Art

Tooth decay is the most common chronic disease for many children and adults. A bacterial biofilm called plaque that develops on teeth contributes to tooth decay. While tooth decay can be prevented or mitigated by regular and proper tooth brushing, many people still develop tooth decay because of improper and inefficient tooth brushing. Dental visit can also prevent and treat tooth decay, but most people have two preventive dental care visits a year and tooth decay can be developed between two dental visits. Thus, there is a need for a frequent and convenient method for continuously monitoring the health of teeth.

SUMMARY OF THE INVENTION

In one embodiment of the present invention, there is provided an electric toothbrush that includes a handle and a brush head attached to one end of the handle. The brush head includes a bristle unit and an ultrasound sensor. The bristle unit cleans teeth and the ultrasound sensor acquires ultrasound data of the teeth.

In another embodiment, the ultrasound sensor emits and receives ultrasound signal at a frequency higher than 20 KHz.

In another embodiment, the ultrasound sensor emits and receives ultrasound signal at a frequency of 20 KHz to 100 MHz, 50 KHz to 50 MHz, or 1 MHz to 20 MHz.

In another embodiment, the ultrasound data of the teeth are sent wireless to a workstation for processing.

In another embodiment, the ultrasound data of the teeth are sent to a workstation for processing via a wire.

In another embodiment, the bristle unit and the ultrasound sensor are attached to a same side of the brush head.

In another embodiment, the ultrasound sensor is attached to the handle, and the bristle unit is detachably slid onto and surrounds the ultrasound sensor.

In another embodiment, the brush head includes a first side and a second side; the bristle unit is attached to the first side of the brush head; and the ultrasound sensor is attached to the second side of the brush head.

In another embodiment, the brush head is an L-shaped brush head; the L-shaped brush head includes a first inside side and a second inside side; the bristle unit is attached to the first inside side of the L-shaped brush head; and the ultrasound sensor is attached to the second inside side of the L-shaped brush head.

In another embodiment, the brush head is a U-shaped brush head; the U-shaped base includes a first inside side and a second inside side; the bristle unit is attached to the first inside side of the U-shaped brush head; and the ultrasound sensor is attached to the second inside side of the U-shaped brush head.

In another embodiment, the brush head is a taco-shaped brush head; the taco-shaped brush head includes a first inside side and a second inside side; the bristle unit is attached to the first inside side of the taco-shaped brush head; and the ultrasound sensor is attached to the second inside side of the taco-shaped brush head.

In one embodiment of the present invention, there is provided a portable tooth decay detection device that includes a handle and an ultrasound sensor attached to one end of the handle. The ultrasound sensor emits and receives ultrasound signal at a frequency of higher than 20 KHz and acquires ultrasound data of teeth.

In another embodiment, the ultrasound data of the teeth are sent wireless to a workstation for processing.

In another embodiment, the ultrasound data of the teeth are sent to a workstation for processing via a wire.

In another embodiment, the ultrasound sensor is detachably attached to the one end of the handle.

In one embodiment of the present invention, there is provided a method for detecting tooth decay that includes providing a portable ultrasound sensor, collecting ultrasound data of teeth via the portable ultrasound sensor, establishing a standard acoustic signature database based on the ultrasound data of the teeth, continuing collecting additional ultrasound data of the teeth, comparing the additional ultrasound data of the teeth against the standard acoustic signature database to detect abnormal data, and providing a warming for tooth decay based on the abnormal data.

In another embodiment, the collecting ultrasound data of the teeth includes emitting and receiving ultrasound signal at a frequency of higher than 20 KHz.

In another embodiment, the collecting ultrasound data of the teeth includes pointing the portable ultrasound sensor directly to occlusal surfaces of the teeth.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings.

Figure 1:
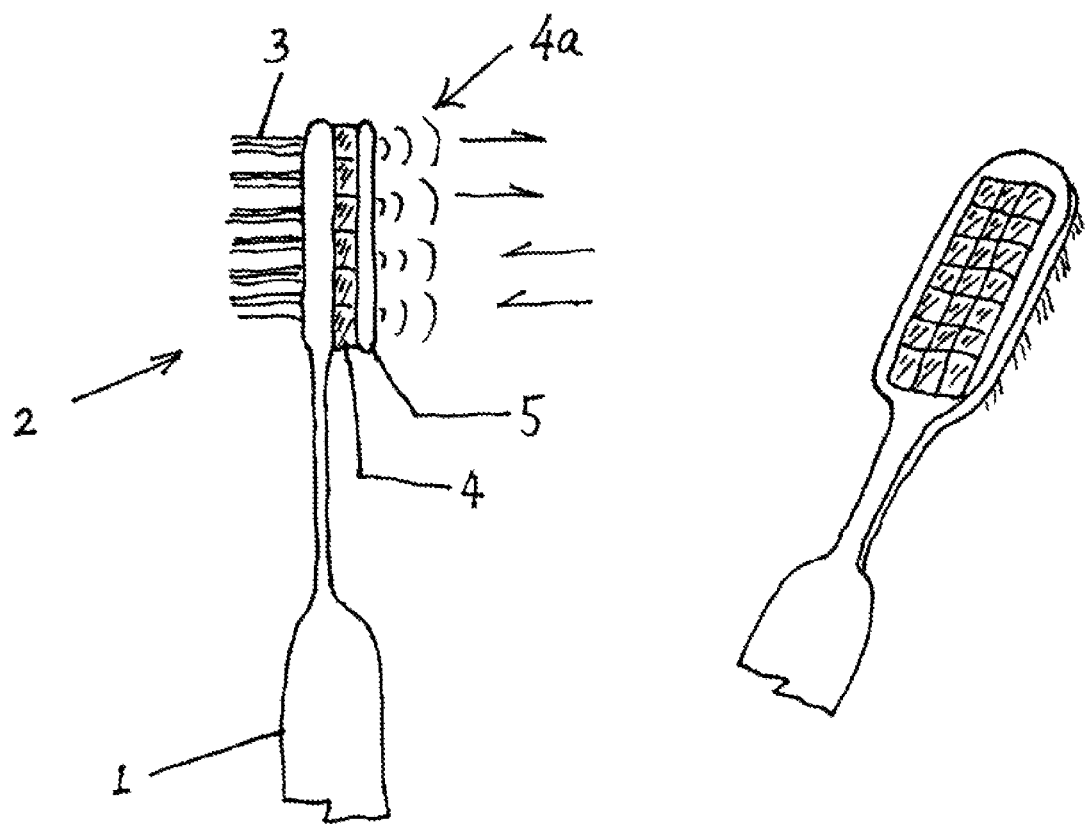
FIG. 1 shows an electric toothbrush with an ultrasound sensor.
Figure 2:
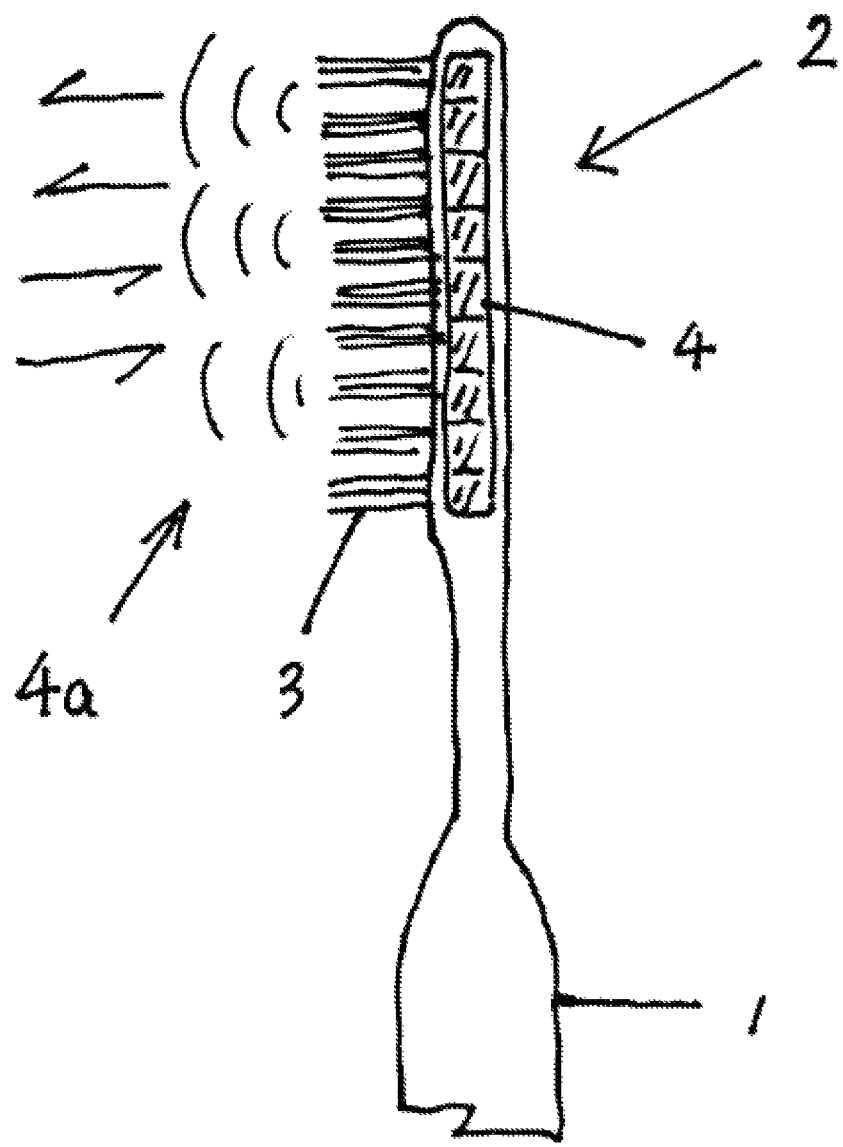
FIG. 2 shows an electric toothbrush with an ultrasound sensor and a bristle unit on the same side of a brush head.

The present invention provides an electric toothbrush. As shown in FIG. 1, the electric toothbrush includes a handle 1 and a brush head 2. The brush head includes a bristle unit 3 and an ultrasound sensor 4. The bristle unit 3 and the ultrasound senor 4 can be on the same side of the brush head 2 (FIG. 2) or on opposite sides of the brush head 2 (FIG. 1). Coupling material 5 can be added to protect the ultrasound sensor 4 (FIG. 1). The ultrasound sensor 4 emits and receives ultrasound signals 4a. The toothbrush further includes a power source and an electric motor. The power source can be a rechargeable battery, and provides power to the electric motor that connects with the bristle unit 3 for cleaning teeth. The power source also provides power to the ultrasound sensor 4. Preferably, the ultrasound signals have a frequency higher than 20 KHz. More preferably the ultrasound signals have a frequency of 20 KHz to 100 MHz, 50 KHz to 50 MHz, or 1 MHz to 20 MHz.

Figure 3:
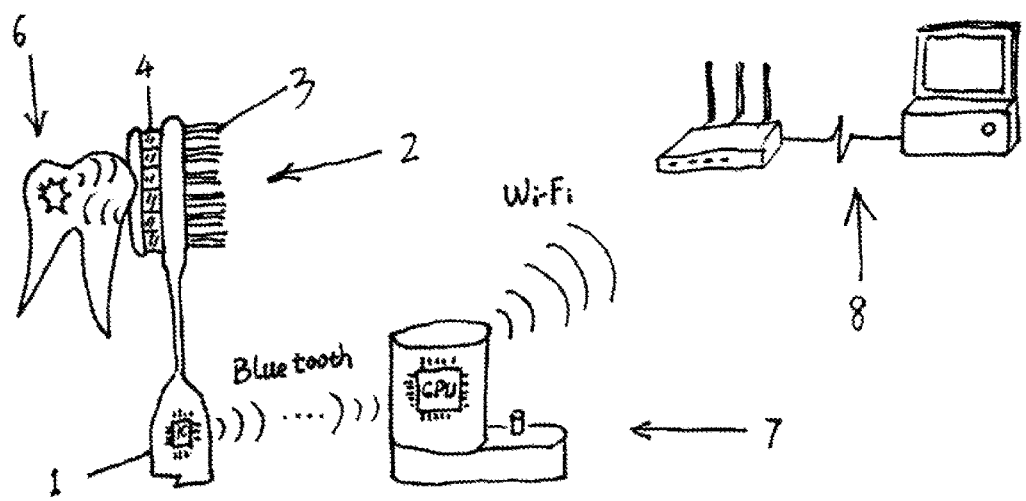
FIG. 3 shows an electric toothbrush with an ultrasound sensor and a bristle unit on opposite side of a brush head.

As shown in FIG. 3, when a user places the electric toothbrush near a tooth 6, the ultrasound sensor 4 emits ultrasound signals to toward the tooth 6, and receives the echo of the ultrasound signals (hereafter, "ultrasound data"). The ultrasound data are then transferred to electric toothbrush base 7 via a wireless connection (e.g., Bluetooth) or wired connection. After receiving the ultrasound data, the electric toothbrush base 7 can store the ultrasound data and then transfer the ultrasound data to a workstation 8 via a wireless connection or wired connection for data processing. The electric toothbrush base 7 can also be the charging station for the electric toothbrush.

Figure 4:
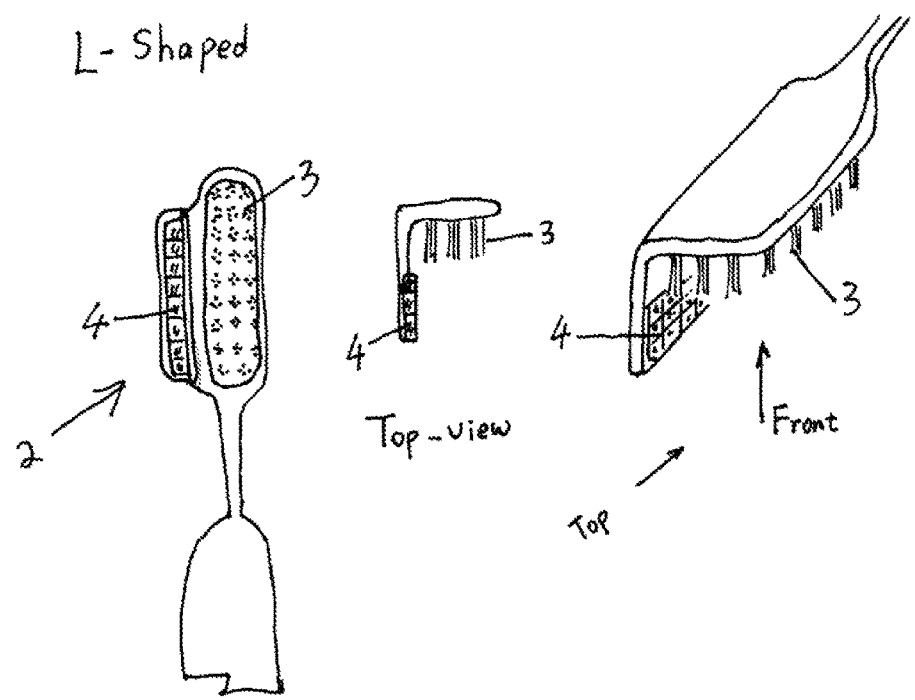
FIG. 4 shows an L-shaped electric toothbrush with an ultrasound sensor.
Figure 5:
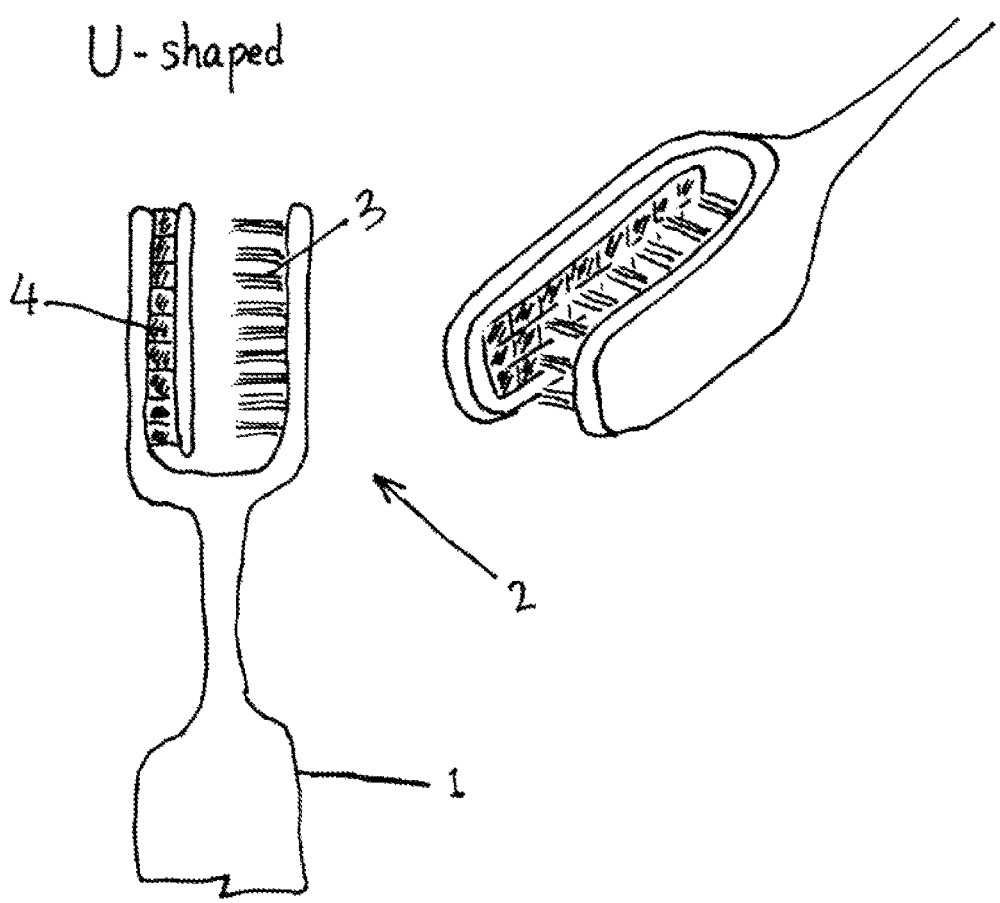
FIG. 5 shows a U-shaped electric toothbrush with an ultrasound sensor.
Figure 6:
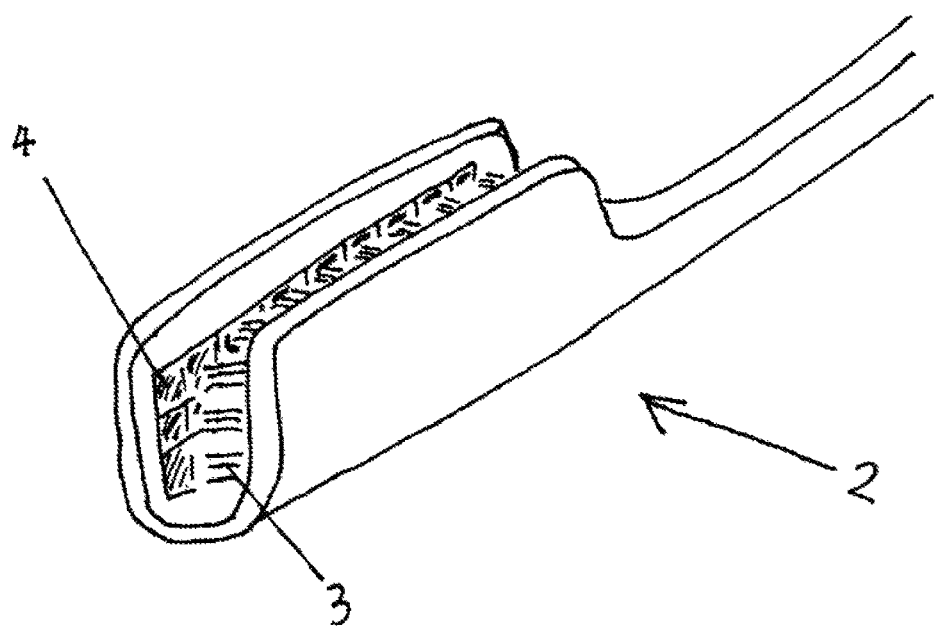
FIG. 6 shows a taco-shaped electric toothbrush with an ultrasound sensor.

The brush head 2 can have various shapes. For example, FIG. 4 shows an L-shaped brush head. The L-shaped brush head includes a first inside side and a second inside side. The bristle unit 3 is attached to the first inside side of the L-shaped brush head, and the ultrasound sensor 4 is attached to the second inside side of the L-shaped brush head. FIG. 5 shows a U-shaped brush head. The U-shaped brush head includes a first inside side and a second inside side. The bristle unit 3 is attached to the first inside side of the U-shaped brush head, and the ultrasound sensor 4 is attached to the second inside side of the U-shaped brush head. FIG. 6 shows a taco-shaped brush head. The taco-shaped brush head includes a first inside side and a second inside side. The bristle unit 3 is attached to the first inside side of the taco-shaped brush head, and the ultrasound sensor 4 is attached to the second inside side of the taco-shaped brush head.

Figure 7:
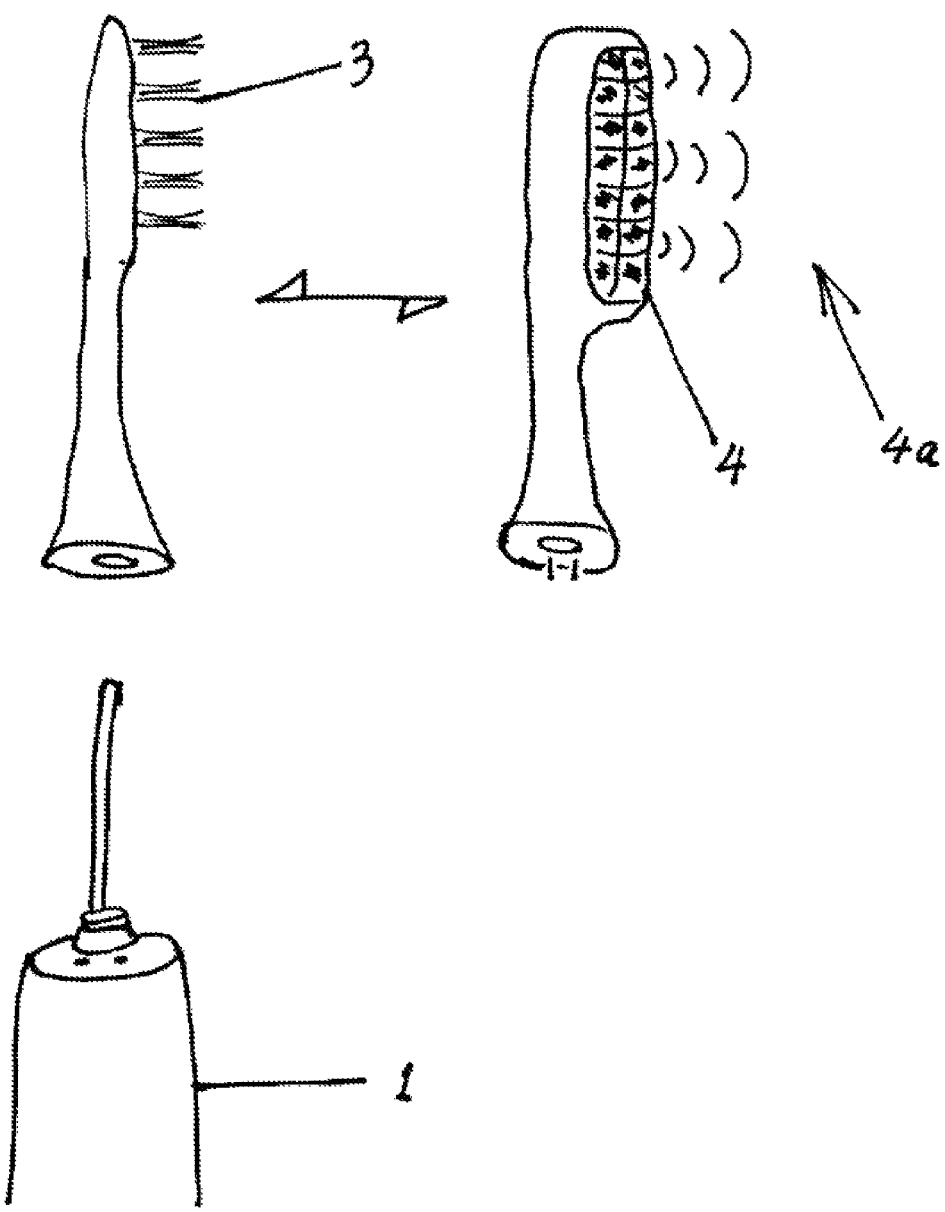
FIG. 7 shows a detachable ultrasound sensor.

FIG. 7 shows an electric toothbrush with a handle 1 and a detachable bristle unit 3. The detachable bristle unit 3 can be replaced by a detachable ultrasound sensor 4, and the ultrasound sensor 4 emits and receives ultrasound signals 4a. In this case, there is provided a portable tooth decay detection device that includes a handle and an ultrasound sensor detachably or permanently attached to one end of the handle. Ultrasound sensor emits and receives ultrasound signals and acquires ultrasound data of teeth. Preferably, the ultrasound signals have a frequency higher than 20 KHz. More preferably the ultrasound signals have a frequency of 20 KHz to 100 MHz, 50 KHz to 50 MHz, or 1 MHz to 20 MHz. The ultrasound data of the teeth are sent wireless or via a wire to a workstation for processing.

Figure 8:
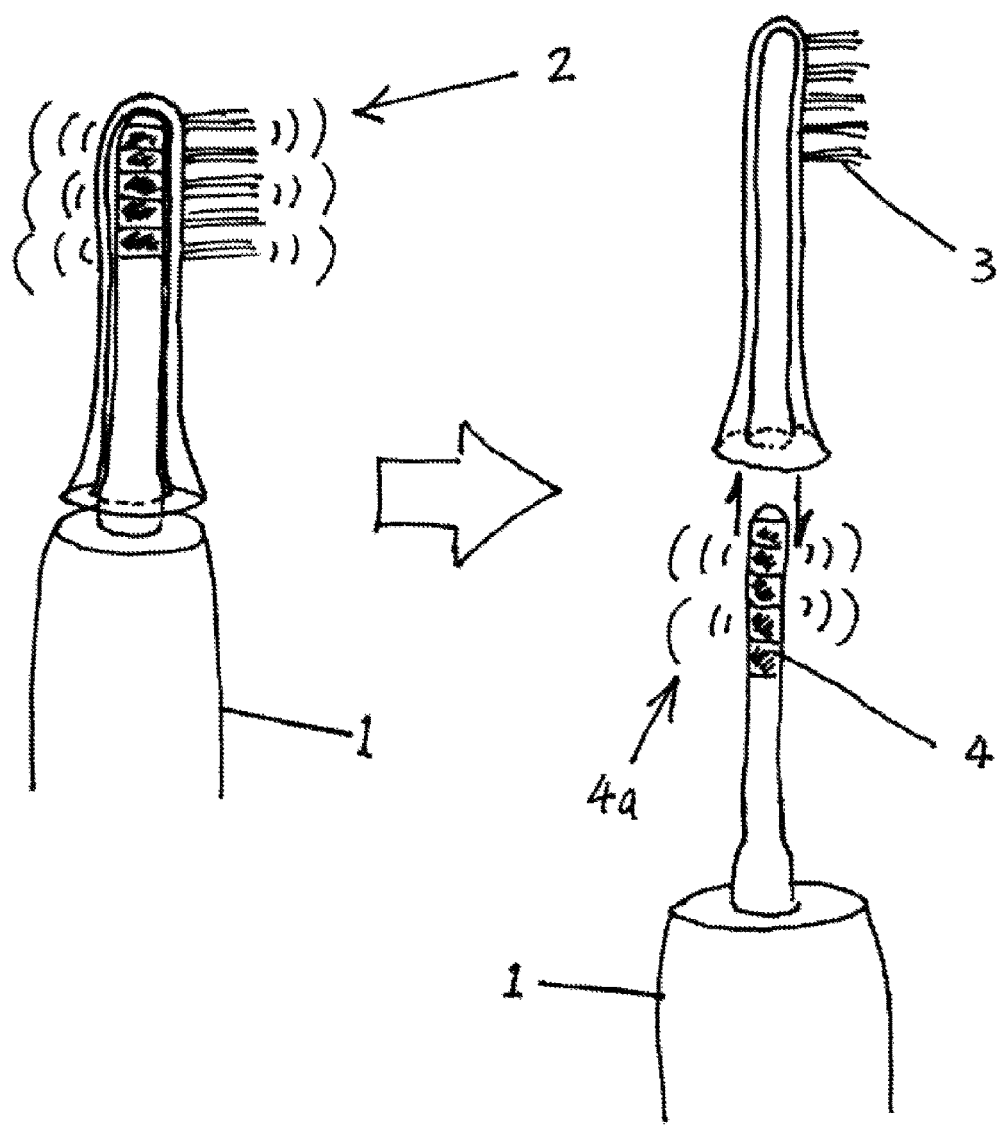
FIG. 8 shows an electric toothbrush with a bristle unit that is detachably slid onto and surrounds an ultrasound sensor

FIG. 8 shows an electric toothbrush with a handle 1 and a brush head 2. The brush head includes a detachable bristle unit 3 and a stick-shaped ultrasound sensor 4. The ultrasound sensor 4 is attached to one end of the handle 1, and emits and receives ultrasound signals 4a. The bristle unit 4 can be detachably slid onto and surround the ultrasound sensor 4.

The electric toothbrush and the portable tooth decay detection device described above provide a method for detecting tooth decay. The method includes providing a portable ultrasound sensor (an electric toothbrush and a portable tooth decay detection device), collecting ultrasound data of teeth via the portable ultrasound sensor, establishing a standard acoustic signature database based on the ultrasound data of the teeth, continuing collecting additional ultrasound data of the teeth, comparing the additional ultrasound data of the teeth against the standard acoustic signature database to detect abnormal data, and providing a warming for tooth decay based on the abnormal data. The collecting ultrasound data of the teeth includes emitting and receiving ultrasound signal at a frequency of higher than 20 KHz. The collecting ultrasound data of the teeth includes pointing the portable ultrasound sensor directly to occlusal surfaces of the teeth.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An electric toothbrush comprising:
a handle; and
a brush head attached to one end of the handle, the brush head including a bristle unit and an ultrasound sensor, wherein the bristle unit cleans teeth and the ultrasound sensor acquires ultrasound data of the teeth; and
wherein the ultrasound sensor is attached to the handle, and the bristle unit is detachably slid onto and surrounds the ultrasound sensor.

\* \* \* \* \*